(12) United States Patent
    Gorski et al.

(10) Patent No.:    US 12,623,073 B2
(45) Date of Patent:     May 12, 2026

(54) IMPLANTABLE BONE GROWTH STIMULATOR

(71) Applicant: Ortho Dynamics LLC, Glastonbury, CT (US)

(72) Inventors: John Gorski, Waterford, MI (US); Jason Gorski, Waterford, MI (US); Daniel J. Mastella, Farmington, CT (US)

(73) Assignee: Ortho Dynamics LLC, Glastonbury, CT (US)

(*) Notice: Subject to any disclaimer, the term of this patent is extended or adjusted under 35 U.S.C. 154(b) by 508 days.

(21) Appl. No.: 17/649,130

(22) Filed: Jan. 27, 2022

(65) Prior Publication Data

US 2023/0233849 A1     Jul. 27, 2023

(51) Int. Cl.
   *A61N 1/32*         (2006.01)
   *A61N 1/372*        (2006.01)
   *A61N 1/40*         (2006.01)

(52) U.S. Cl.
   CPC ......... *A61N 1/326* (2013.01); *A61N 1/37229* (2013.01); *A61N 1/37282* (2013.01); *A61N 1/40* (2013.01)

(58) Field of Classification Search
   CPC ............... A61N 1/326; A61N 1/37229; A61N 1/37282; A61N 1/40; A61N 1/205; A61N 1/3787
   See application file for complete search history.

(56) References Cited

U.S. PATENT DOCUMENTS

| | | | |
|---|---|---|---|
| 5,441,527 A | | 8/1995 | Erickson et al. |
| 6,120,502 A | * | 9/2000 | Michelson ............ A61F 2/4455 |
| | | | 606/279 |
| 6,778,861 B1 | * | 8/2004 | Liebrecht ............ A61C 8/0007 |
| | | | 607/51 |
| 7,890,179 B2 | | 2/2011 | Wiegmann et al. |
| 8,078,283 B2 | | 12/2011 | Cowan et al. |
| 9,327,115 B2 | | 5/2016 | Neuman et al. |
| 9,474,908 B2 | | 10/2016 | Hirschl |
| 10,362,982 B2 | | 7/2019 | Stevenson et al. |

(Continued)

FOREIGN PATENT DOCUMENTS

| | | |
|---|---|---|
| WO | 2018200723 A1 | 11/2018 |
| WO | 2019183622 A1 | 9/2019 |

OTHER PUBLICATIONS

Texas Instruments, RF340 Family User's Guide, 2012, p. 53 (Year: 2023).*

(Continued)

*Primary Examiner* — Catherine M Voorhees
(74) *Attorney, Agent, or Firm* — Mindful IP PLLC

(57) ABSTRACT

A bone growth stimulator includes an antenna configured to receive electromagnetic signals in a radio frequency band, and a controller having a power source including a supercapacitor electrically connected to the antenna. The supercapacitor stores a charge in accordance with the electromagnetic signals received by the antenna. The bone growth stimulator further includes a cathode extending from the controller to a desired location of bone growth and an anode electrically connected to the power source and extending from the controller. Electrical energy travelling from the anode to the cathode stimulates bone growth in a patient.

9 Claims, 7 Drawing Sheets

(56) References Cited

U.S. PATENT DOCUMENTS

| | | | |
|---|---|---|---|
| 10,363,412 | B2 | 7/2019 | Leuthardt et al. |
| 10,596,384 | B2 | 3/2020 | Gellman et al. |
| 2001/0032666 | A1* | 10/2001 | Jenson .................. C23C 16/047 |
| | | | 438/57 |
| 2007/0293912 | A1* | 12/2007 | Cowan ................... A61N 1/326 |
| | | | 607/51 |
| 2008/0255556 | A1* | 10/2008 | Berger ................... A61N 1/326 |
| | | | 606/301 |
| 2009/0062886 | A1 | 3/2009 | O'Handley et al. |
| 2010/0298886 | A1 | 11/2010 | Kraus et al. |
| 2011/0238132 | A1 | 9/2011 | Madjar et al. |
| 2012/0059434 | A1 | 3/2012 | Nycz |
| 2013/0066426 | A1 | 3/2013 | Martinson et al. |
| 2013/0282070 | A1 | 10/2013 | Cowan et al. |
| 2015/0207484 | A1 | 7/2015 | Stevenson et al. |
| 2015/0367130 | A1* | 12/2015 | Walraevens ....... A61N 1/36038 |
| | | | 607/57 |
| 2016/0270927 | A1* | 9/2016 | Zellmer ............... A61B 5/4566 |
| 2017/0157407 | A1 | 6/2017 | Zellmer et al. |
| 2018/0028320 | A1 | 2/2018 | Forsell |
| 2018/0310964 | A1* | 11/2018 | Stevenson .......... A61B 17/7049 |
| 2019/0008386 | A1* | 1/2019 | Puryear ............... A61B 5/4851 |
| 2019/0009083 | A1 | 1/2019 | Webster et al. |
| 2019/0060645 | A1 | 2/2019 | Kearns |
| 2019/0104936 | A1* | 4/2019 | Gunn ..................... A61B 5/076 |
| 2019/0224022 | A1 | 7/2019 | Zellmer et al. |
| 2019/0351223 | A1 | 11/2019 | Walser et al. |
| 2020/0038676 | A1* | 2/2020 | Rogachefsky ........... A61N 2/02 |
| 2020/0108252 | A1* | 4/2020 | Zellmer .................. A61F 2/482 |
| 2020/0297400 | A1* | 9/2020 | Lee .................... A61B 17/8028 |
| 2021/0361965 | A1* | 11/2021 | Yakobson ................ A61N 2/02 |
| 2022/0168579 | A1* | 6/2022 | Robinson .............. H10N 35/00 |
| 2023/0346440 | A1* | 11/2023 | Adler .................. A61B 5/4504 |
| 2024/0015456 | A1* | 1/2024 | Djalilian ............. H04R 25/606 |

OTHER PUBLICATIONS

Rebecca A Bercich et al., "Far-Field RF Powering of Implantable Devices: Safety Considerations", Aug. 2013, IEEE Transactions on Biomedical Engineering, vol. 60, No. 8, pp. 2107-2112 (Year: 2013).*

Keller, R. B. (2023). Design for electromagnetic compatibility—in a nutshell: Theory and practice. Springer Nature. 2023. https://link.springer.com/book/10.1007/978-3-031-14186-7.

* cited by examiner

IMPLANTABLE BONE GROWTH STIMULATOR

BACKGROUND

Bone fractures can be the result of trauma, overuse, or certain diseases that weaken bone structure. Traditional methods of healing bone fractures involve aligning the bone segments and limiting motion at the fracture site until the bone heals. Often times, individuals with a bone fracture must wear a cast or splint until healing is complete.

DETAILED DESCRIPTION

Traditional methods of bone healing using a cast or using a splint to limit motion takes a long time. On average, healing a bone can take weeks or months or may ultimately not heal at all. Stimulating the area with electromagnetic energy, however, can expedite bone healing. Applying electromagnetic energy directly to a fractured bone requires surgically implanting a bone stimulating device. Traditional bone stimulating devices are physically connected to a power supply implanted in the patient's body via a wire. The power supply limits the effectiveness of the direct bone stimulator.

One solution is a bone growth stimulator that can be powered wirelessly. For example, a bone growth stimulator may include an antenna configured to receive electromagnetic signals in a radio frequency band, and a controller having a power source including a supercapacitor electrically connected to the antenna. The supercapacitor stores a charge in accordance with the electromagnetic signals received by the antenna. The bone growth stimulator further includes a cathode extending from the controller to a desired location of bone growth and an anode electrically connected to the power source and extending from the controller. Electrical energy travelling from the anode to the cathode stimulates bone growth in a patient.

The elements shown may take many different forms and include multiple and/or alternate components and facilities. The example components illustrated are not intended to be limiting. Indeed, additional or alternative components and/or implementations may be used. Further, the elements shown are not necessarily drawn to scale unless explicitly stated as such.

Figure 1:
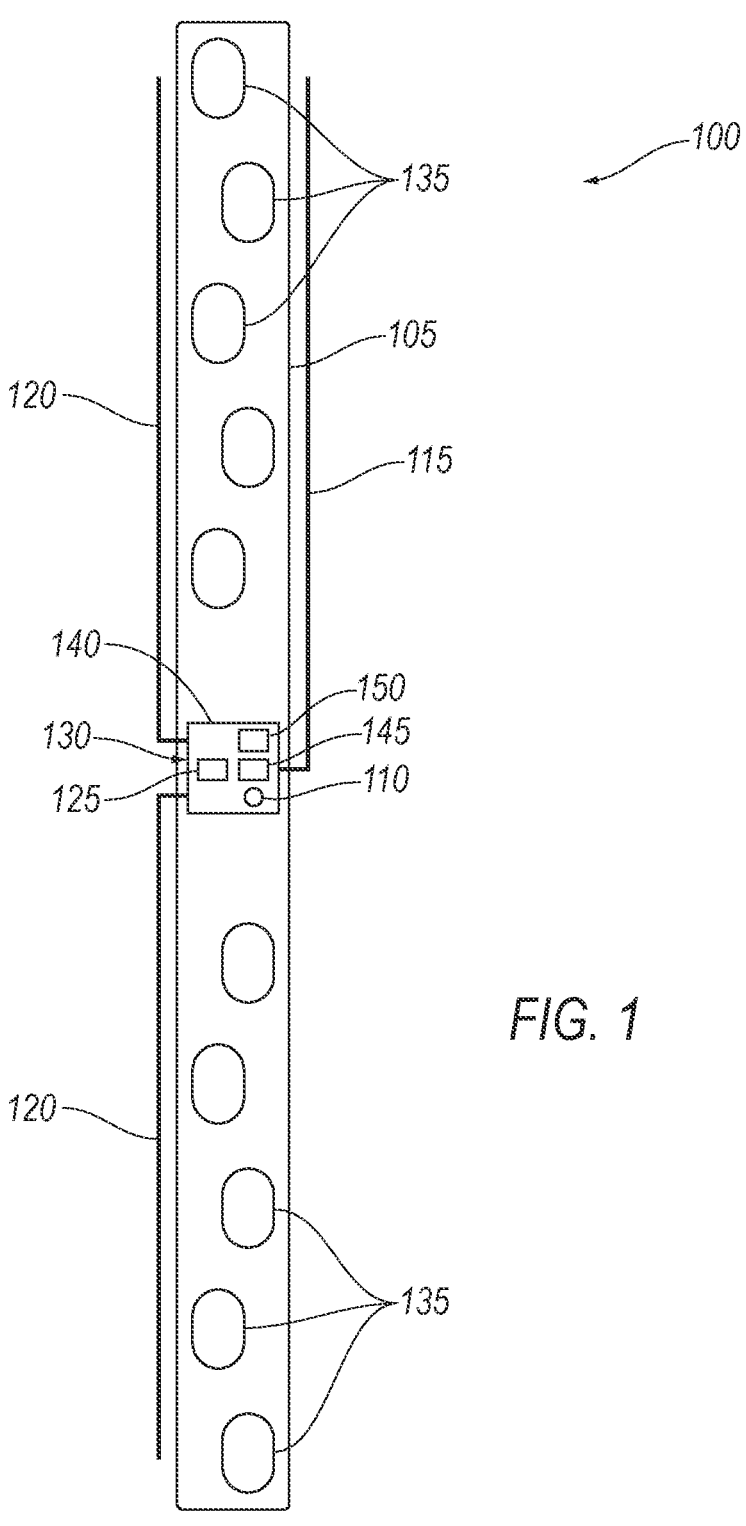
FIG. 1 illustrates an example bone growth stimulator.

As illustrated in FIG. 1, an example bone growth stimulator 100 includes a body 105, a cathode 110, an anode 115, an antenna 120, a power source 125, and a controller 130.

The components can be assembled to form the bone growth stimulator 100, which can be surgically implanted in a patient to stimulate bone growth.

The body 105 shown in FIG. 1 takes the form of a metal plate. The body 105 may be formed from a material approved for implantation in a human or animal body 105. Example materials for the body 105 may include stainless steel, titanium, or carbon fiber. As shown in FIG. 1, the body 105 has a generally rectangular shape with a length of approximately 1-18 inches and a width of approximately 0.25-4 inches depending on the bone on which the bone growth stimulator 100 will be implanted and whether the bone growth stimulator 100 is to be used to heal a human bone or an animal bone. For instance, a larger body 105 may be used on larger human bones or bones of large animals such as horses or cows. The body 105 may define holes 135 for receiving bone screws or other fasteners that can be used to attach the body 105 to a person or animal.

The cathode 110 is a negatively charged terminal extending from the controller 130. When the bone growth stimulator 100 is implanted in a patient, the cathode 110 may be placed on the part of the bone where growth is desired. In some instances, the cathode 110 is a conductive wire extending from the controller 130. In other instances, the cathode 110 is an exposed conductive pad, such as a copper pad, on the controller 130. The type of cathode 110 used may depend upon the design of the body 105, where the bone fracture occurred, and so on. For instance, the cathode 110 may be a wire in instances where it is impossible or impractical for a conductive pad on the controller 130 to be in physical contact with the site of the bone fracture. Alternatively, having the cathode 110 take the form of the conductive pad may be more suitable for instances where the conductive pad can be placed in physical contact with the site of the bone fracture. To increase the likelihood of uniform bone stimulation, multiple anodes 115 may be incorporated into the bone growth stimulator 100.

The anode 115 is a positively charged terminal extending from the controller 130 and, when implanted in a patient, into the patient's soft tissue near the surgical site. In some instances, the anode 115 takes the form of a conductive wire electrically connected to the power source 125. As such, the positive charge of the anode 115 originates from the power source 125 and enters the patient's soft tissue. The circuit is completed when the current from the anode 115 travels through the soft tissue and through a section of the patient's bone to the cathode 110. As discussed above, the cathode 110 is in physical contact with the part of the bone where growth is desired. The current, therefore, stimulates bone growth as it travels from the anode 115 to the cathode 110. To increase the likelihood of uniform bone stimulation, multiple anodes 115 may be incorporated into the bone growth stimulator 100.

The antenna 120 is a metal conductor, such as a wire, or a flexible printed circuit board disposed on the body 105 of the bone growth stimulator 100. The antenna 120 may have a length for receiving electromagnetic signals in the radio frequency band. For instance, the antenna 120 may have a length that allows the antenna 120 to receive signals ranging from approximately 20 kilohertz to approximately 300 gigahertz. In some instances, the antenna 120 is coiled so it may fit on the body 105 of the bone growth stimulator 100 or in the surgical site. The antenna 120 may be electrically connected to the controller 130 so, e.g., radio frequency energy captured by the antenna 120 can be used to inductively charge the power source 125.

The power source 125 is disposed on the controller 130 and is configured to store electrical energy. In some instances, the power source 125 is a supercapacitor such as an electrostatic double-layer capacitor, an electrochemical pseudocapacitor, or a hybrid capacitor such as a lithium-ion capacitor. The power source 125 outputs a DC signal on the order of approximately 5-100 micro Amps to the anode 115 to stimulate bone growth. The power source 125 is charged by the radio frequency energy captured by the antenna 120. For example, when a radio frequency transmitter 160 (see FIG. 5) is brought near (e.g., within approximately 80 feet of) the bone growth stimulator 100, radio frequency signals transmitted by the transmitter 160 are received by the antenna 120. Energy from the radio frequency signals is stored in the power source 125.

The controller 130 may be a microprocessor-based controller 130 implemented via circuits, chips, or other electronic components disposed on a printed circuit board 140. The controller 130 includes a memory 145 and a processor 150, and possibly other electronic components. The printed circuit board 140 is a laminated structure having insulated and conductive layers. In some instances, the printed circuit board 140 is flexible. For instance, the printed circuit board 140 may be formed from a thin, flexible, insulating polymer film. Components of the controller 130 and the bone growth stimulator 100 may be soldered to or otherwise electrically connected or attached to the printed circuit board 140. Connections between various components of the controller 130 and the bone growth stimulator 100 may be made through traces or planes etched or otherwise incorporated into the printed circuit board 140.

The memory 145 is implemented via circuits, chips or other electronic components and can include one or more of read only memory (ROM), random access memory (RAM), flash memory, electrically programmable memory (EPROM), electrically programmable and erasable memory (EEPROM), embedded MultiMediaCard (eMMC), or any volatile or non-volatile media etc. The memory 145 may store instructions executable by the processor 150 and data such as historical data concerning the charging or discharging of the power source 125, the amount of time the anode 115 was energize over a period of time, patient identification information, information about the manufacture of the bone growth stimulator 100, information about when the bone growth stimulator 100 was implanted, and so on. The instructions and data stored in the memory 145 may be accessible to the processor 150 and possibly other components of the bone growth stimulator 100.

The processor 150 is implemented via circuits, chips, or other electronic component and may include one or more microcontrollers, one or more field programmable gate arrays (FPGAs), one or more application specific integrated circuits (ASICs), one or more digital signal processors (DSPs), one or more customer specific integrated circuits, etc. The processor 150 executes the instructions stored in the memory 145 to, e.g., control the operation of the bone growth stimulator 100. For instance, the processor 150 may be programmed to cause the power source 125 to periodically or continuously energize the anode 115 or inductively store radio frequency energy received by the antenna 120. That is, the processor 150 may be programmed to cause the supercapacitor to inductively store a charge in accordance with the electromagnetic signals received by the antenna 120. In some instances, the processor 150 or another component of the controller 130 includes a rectifier for modifying the signal received from the antenna 120. For instance, if the signal received from the antenna 120 is an alternating current (AC) signal, the processor 150 may include an AC to DC rectifier to convert the AC signal received by the antenna 120 into a direct current (DC) signal appropriate for charging the power source 125.

In some possible implementations, the bone growth stimulator 100 may be configured for one- or two-way wireless communication to allow, e.g., the processor 150 to communicate status updates, receive updated stimulation parameters, or both. For instance, the bone growth stimulator 100 may communicate information such as battery life, on/off status, runtime, total healing time, etc. In some possible approaches, the wireless communication may be between components of the bone growth stimulator 100 and the remote transmitter 160 (see FIG. 5). Alternatively or in addition, the bone growth stimulator 100 may wirelessly communicate with a remote device.

Figure 2:
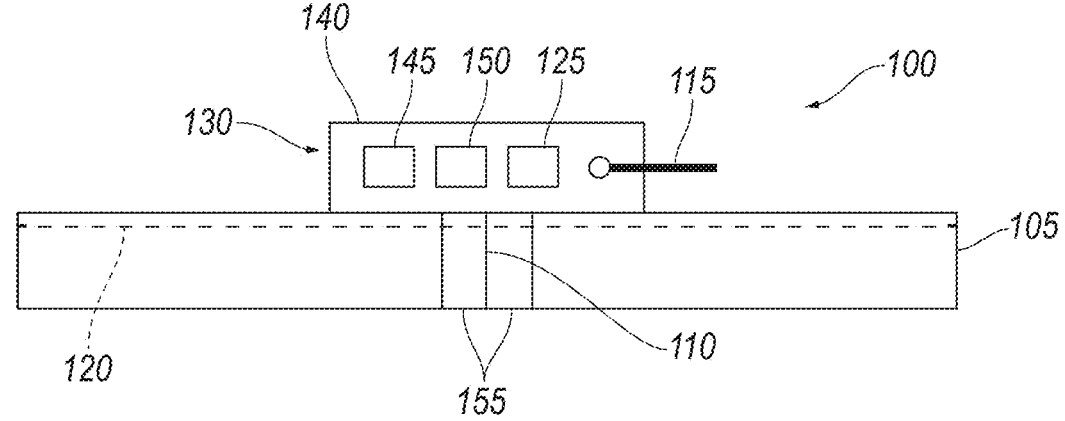
FIG. 2 illustrates a side view of the example bone growth stimulator of FIG. 1.

FIG. 2 illustrates a side view of the example bone growth stimulator 100 of FIG. 1. The dimensions of the bone growth stimulator 100 are exaggerated for purposes of clarity and illustration. For surgical implantation, the bone growth stimulator 100 may be as small as possible.

In the example of FIG. 2, the body 105 defines a hole, and the cathode 110 extends from the printed circuit board 140 to the fractured bone through the hole in the body 105. A body-safe epoxy or other filler 155 may be used to insulate the cathode 110 from coming into electrical contact with the body 105 of the bone growth stimulator 100. The anode 115 extends from another side of the printed circuit board 140 so that it may electrically contact the patient's soft tissue.

With further reference to the example of FIG. 2, the antenna 120 is embedded into the body 105 of the bone growth stimulator 100. The antenna 120 extends along the length of the body 105 to maximize the range of radio frequency energy absorption. Depending on the wavelength of the radio frequency signal, the antenna 120 may be coiled.

Figure 3:
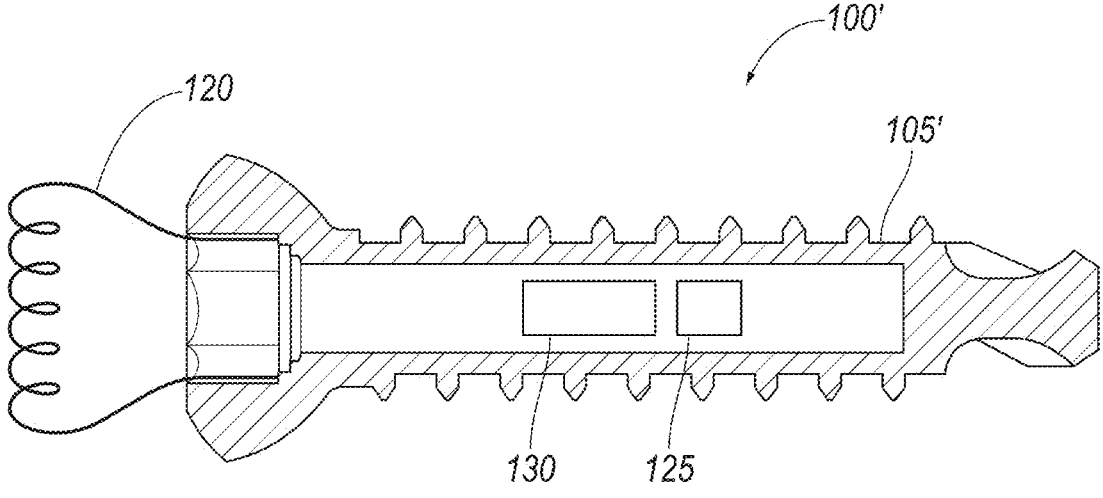
FIG. 3 illustrates a partial cross-sectional view of another example bone growth stimulator.

FIG. 3 illustrates a partial cross-sectional view of another example bone growth stimulator 100. In this example, the body 105 takes the form of a hollow bone screw. In this example of the bone growth stimulator 100, the controller 130 and power source 125 are located in the hollow part of the bone screw. The antenna 120 extends from the controller 130 to an area outside the bone growth stimulator 100. The antenna 120 may also be electrically isolated from the body 105 so radio frequency energy captured by the antenna 120 can be efficiently provided to the power source 125.

The anode 115 and cathode 110 are electrically isolated from the body 105 and from one another. The anode 115 extends from the controller 130 through the body 105 and is electrically connected to the bone on one side of the bone screw. The cathode 110 extends from the controller 130 through the body 105 and is electrically connected to the bone at another location some distance away from the anode 115. For example, the cathode 110 and anode 115 may extend through the bone screw on opposite sides to maximize the distance current will travel through the bone. To increase the likelihood of uniform bone stimulation, multiple anodes 115 and cathodes 110 may be incorporated into the bone screw.

Figure 4:
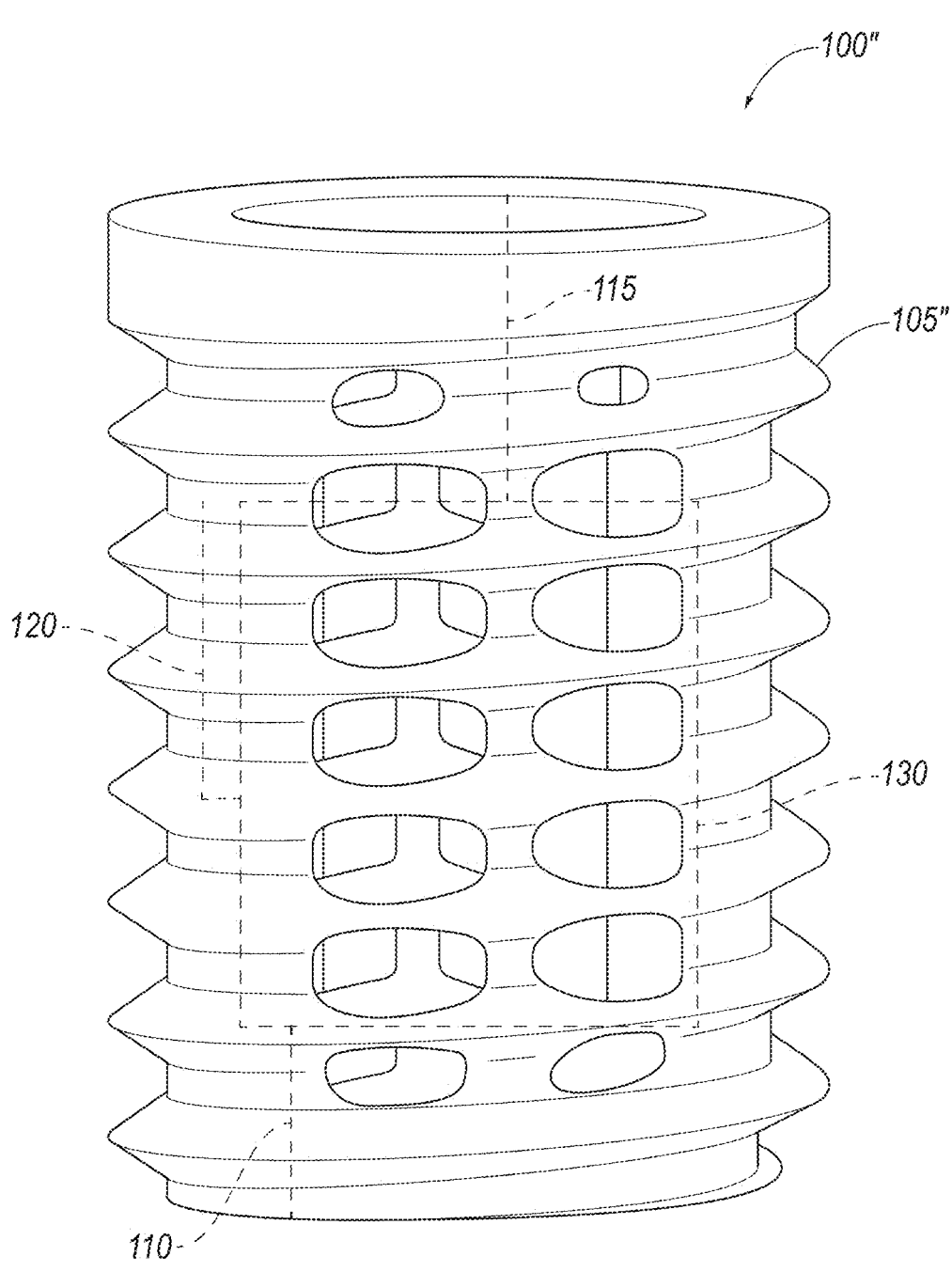
FIG. 4 illustrates a perspective view of another example bone growth stimulator.

FIG. 4 illustrates a perspective view of another example bone growth stimulator 100. In this example, the body 105 takes the form of a spinal cage. While a screw-in spinal cage is shown in FIG. 4, the body 105 may take the form of any other type of apparatus used for spinal fusion.

In the example bone growth stimulator 100 of FIG. 4, the controller 130 and power source 125 are located in the hollow part of the spinal cage. The antenna 120 extends from the controller 130 to an area outside the bone growth stimulator 100. The antenna 120 may also be electrically isolated from the body 105 so radio frequency energy captured by the antenna 120 can be efficiently provided to the power source 125.

The anode 115 and cathode 110 are electrically isolated from the body 105 and from one another. The anode 115 extends from the controller 130 through holes 135 in the body 105 and is electrically connected to the bone on one side of the spinal cage. The cathode 110 extends from the controller 130 through holes 135 in the body 105 of the spinal cage and is electrically connected to the bone at another location some distance away from the anode 115. For example, the cathode 110 and anode 115 may extend through the spinal cage on opposite sides to maximize the distance current will travel through the bone. To increase the likelihood of uniform bone stimulation, multiple anodes 115 and cathodes 110 may be incorporated into the spinal cage.

Figure 5:
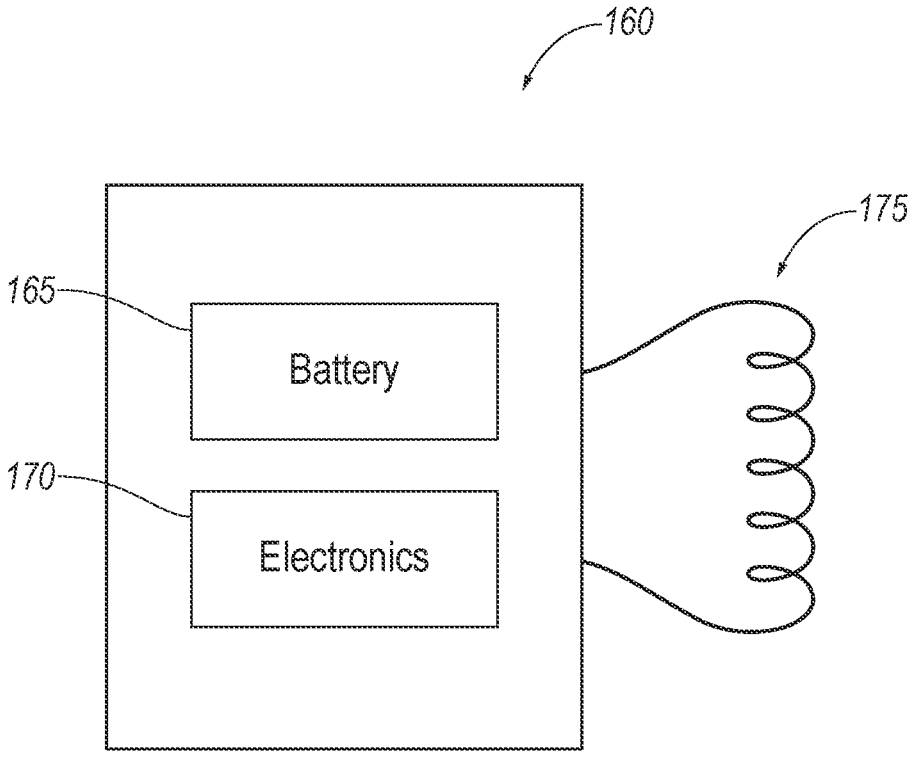
FIG. 5 illustrates an example transmitter used to energize the bone growth stimulator.
Figure 8:
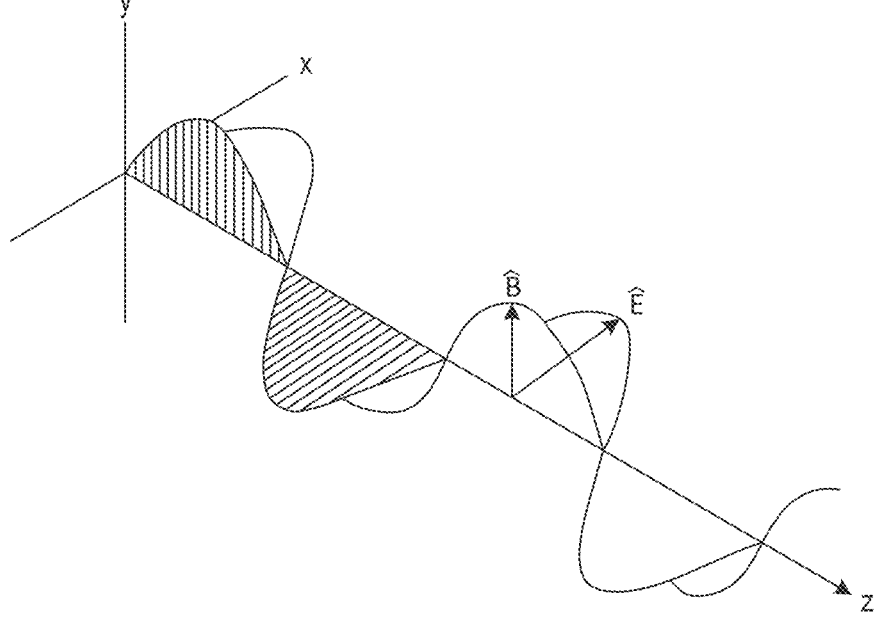
FIG. 8 illustrates the electric field vector (E-field) perpendicular to the magnetic field vector (B-field) in a far-field region.

FIG. 5 illustrates an example remote transmitter 160 used to energize the bone growth stimulator 100. The remote transmitter 160 allows the bone growth stimulator 100 to be charged wirelessly, specifically, without the need for wires to extend outside of the patient's body. For instance, the remote transmitter 160 may be implemented by an over-the-air, far field radio frequency charger configured to provide power transmission through radio waves in the far-field region, up to, e.g., 80 feet where the electric field vector E and magnetic field vector B of an electromagnetic wave are perpendicular to one another. The transmitter 160, as shown, includes a battery 165, control electronics 170, and a transmission coil 175. FIG. 8 shows the electric field vector E and the magnetic field vector B perpendicular to each other in the far-field region.

The battery 165 includes a source of direct current (DC) electrical energy. The battery 165 may include one or more electrochemical cells. The battery 165 includes terminals, each associated with a positive or negative charge. An electric potential exists between the terminals. When connected to the control electronics 170, the transmission coil 175, or both, voltage flows from one terminal of the battery 165, through the control electronics 170 and/or transmission coil 175, and back to the battery 165 through the other terminal.

The control electronics 170 are implemented via circuits, chips, or other electronic components that control operation of the transmitter 160. In some instances, the control electronics 170 include a switch or transistor that selectively connects one or both terminals of the battery 165 to the transmission coil 175. The control electronics 170 may include other electronic devices such as an integrated circuit. For instance, the integrated circuit may implement a timer to automatically connect one or both terminals of the battery 165 to the transmission coil 175 for predetermined intervals of time, e.g., in response to a user input. The user input may include a user pressing a physical or virtual button located on the transmitter 160.

The transmission coil 175 may include a metal wire that generates radio frequency energy to inductively charge the bone growth stimulator 100 when, e.g., the transmission coil 175 is electrically connected to both terminals of the battery 165. For instance, when a user of the transmitter 160 presses a button, the control electronics 170 may close one or more switches to direct current to flow from the battery 165 to the transmission coil 175. The current through the transmission coil 175 may create an electromagnetic field in, e.g., the radio frequency spectrum. When placed within range of the bone growth stimulator 100, the electromagnetic field generated by the transmission coil 175 may be inductively coupled to the antenna 120 of the bone growth stimulator 100. As discussed above, the antenna 120 may use the radio frequency transmissions of the transmission coil 175 to power the controller 130 of the bone growth stimulator 100 and/or charge the power source 125 of the bone growth stimulator 100.

The transmitter 160 may further include a mobile device with a touch-sensitive display screen presenting a graphical user interface. The graphical user interface may present information to the user such as the battery life of the battery 165 of the transmitter 160, the battery life of the power source 125 of the bone growth stimulator 100, patient information, historical information (e.g., how long the bone growth stimulator 100 has been in operation), and other information associated with the operation of the bone growth stimulator 100.

Figure 6A:
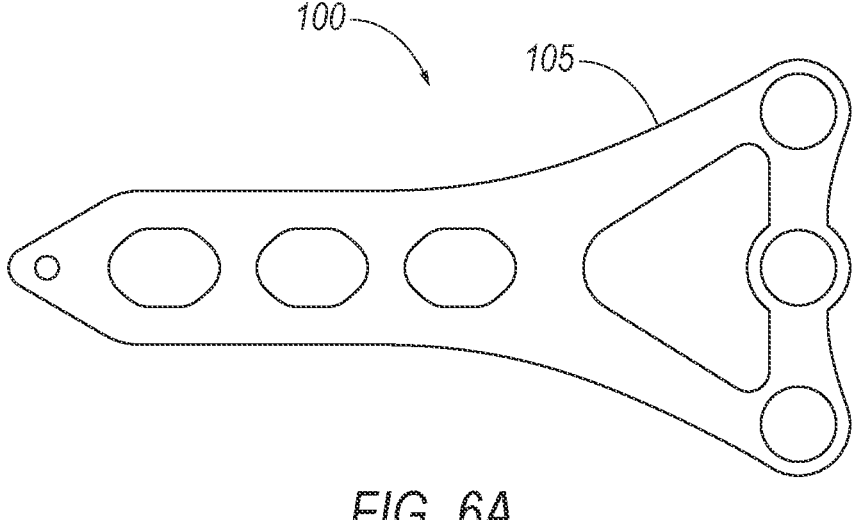
FIGS. 6A-6B illustrate other example bodies that may be used with the bone growth stimulator.
Figure 6B:
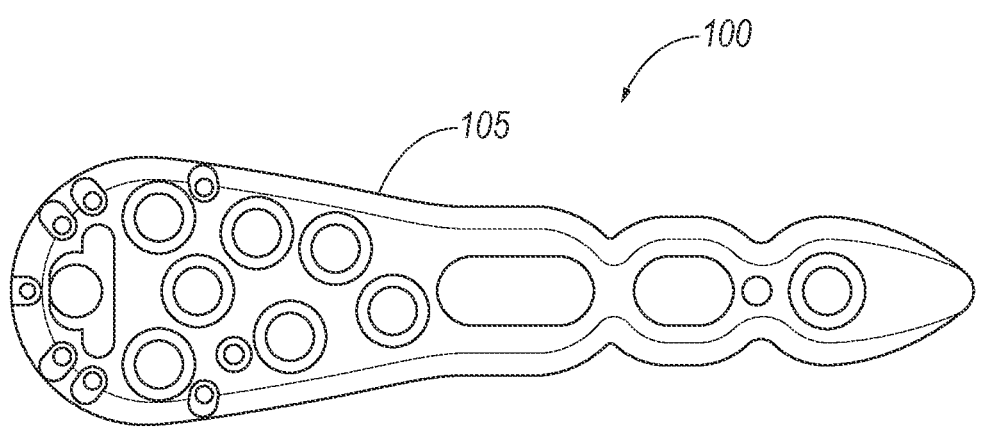

Referring now to FIGS. 6A-6B, the foregoing bone growth stimulator 100 may be incorporated into many different types of surgical plates. In FIGS. 6A and 6B, the body 105 of the bone growth stimulator 100 takes the form of a locking plate having a tapered outer periphery. The body 105 defines holes 135 for receiving bone screws. The controller 130 may be disposed on the body 105 or located within one of the bone screws, as discussed above.

Figure 7:
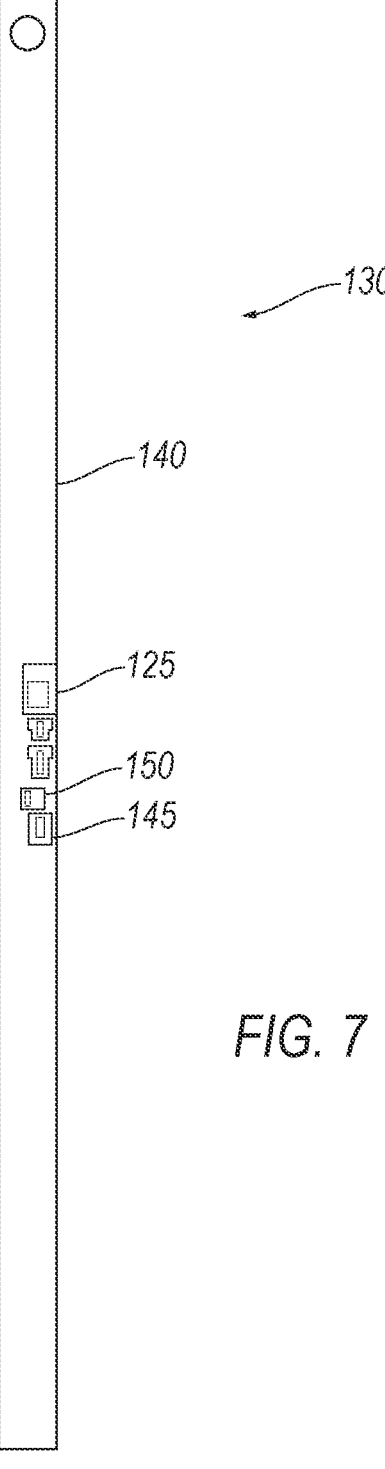
FIG. 7 illustrates another example controller that may be used with the bone growth stimulator.

FIG. 7 illustrates an example controller 130 having an elongated form factor for attaching to the body 105 shown in FIGS. 1-2. In this example approach, the printed circuit board 140 may have dimensions shorter than the length of the body 105 and thinner than the width of the body 105. That way, the controller 130 may be disposed on the body 105 without blocking any of the holes 135 defined by the body 105.

In some instances, the bone growth stimulator 100 may omit the body 105 altogether, or the body 105 may be something other than a surgical plate. For example, the body 105 may be a piece of body-safe plastic or another material separate from the surgical plate. In another possible approach, the printed circuit board 140, for instance, may serve as the body 105. In such instances, the bone growth stimulator 100 may be surgically implanted into the patient at or near the location of the surgical plate. In some possible implementations, the bone growth stimulator 100 may be inserted into the patient, and function, without a surgical plate.

In general, the computing systems and/or devices described may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, California), the AIX UNIX operating system distributed by International Business Machines of Armonk, New York, the Linux operating system, the OS X, macOS, and iOS operating systems distributed by Apple Inc. of Cupertino, California, the BlackBerry OS operating system distributed by Blackberry, Ltd. of Waterloo, Canada, and the Android operating system developed by Google, Inc. and the Open Handset Alliance. Examples of computing devices include, without limitation, a computer workstation, a server, a desktop, notebook, laptop, or handheld computer, or some other computing system and/or device.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. Some of these applications may be compiled and executed on a virtual machine, such as the Java Virtual Machine, the Dalvik virtual machine, or the like. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A bone growth stimulator comprising:

a body configured to have a first surface directly in contact with a bone when implanted;

a printed circuit board attached to the body on a second surface opposite the first surface;

an antenna configured to harvest far field electromagnetic signals from a transmitter in a radio frequency band, wherein an electric field vector E and a magnetic field vector B of the far field electromagnetic signals are perpendicular to each other;

a controller attached to the printed circuit board and having a power source including a supercapacitor, the controller being electrically connected to the antenna, wherein the controller causes the supercapacitor to store a charge in accordance with energy captured from the far field electromagnetic signals harvested by the antenna;

a cathode extending from the controller through the body and configured to be directly contacting the bone; and an anode electrically connected to the power source and extending from the controller, wherein: electrical energy travelling from the anode to the cathode stimulates bone growth in a patient;

both the cathode and the anode are electrically isolated from the body, and a frequency of the far field electromagnetic signals received by the antenna is greater than 800 megahertz and less than 300 gigahertz, and a distance between the transmitter and the bone growth stimulator is greater than one meter and less than 80 feet.

2. The bone growth stimulator of claim 1, wherein the controller is programmed to cause the supercapacitor to store the energy of the far field electromagnetic signals harvested by the antenna.

3. The bone growth stimulator of claim 1 wherein the body is a bone plate, the printed circuit board is attached directly to the bone plate on the second surface and the bone plate is formed from at least one of stainless steel, titanium, and carbon fiber.

4. The bone growth stimulator of claim 1, wherein the body is in a form of a hollow surgical screw formed from at least one of stainless steel, titanium, and carbon fiber.

5. The bone growth stimulator of claim 1, wherein the body includes a spinal cage formed from at least one of stainless steel, titanium, and carbon fiber.

6. The bone growth stimulator of claim 3, wherein the antenna is a metal conductor or a flexible printed circuit board disposed on the bone plate.

7. The bone growth stimulator of claim 3, wherein the antenna is embedded in the bone plate.

8. The bone growth stimulator of claim 4 wherein the antenna is electrically isolated from the body and extends from the controller to an area outside of the body.

9. The bone growth stimulator of claim 5, wherein the antenna is electrically isolated from the body and extends from the controller to an area outside the body.

\* \* \* \* \*